United States Patent [19]

Hayashi et al.

[11] Patent Number: 5,629,748
[45] Date of Patent: May 13, 1997

[54] VISUAL FUNCTION EXAMINATION APPARATUS INCLUDING BINOCULAR FIXATION TARGET

[75] Inventors: Akihiro Hayashi, Toyokawa; Yasumi Hikosaka, Gamagori, both of Japan

[73] Assignee: Nidek Co., Ltd., Japan

[21] Appl. No.: 504,111

[22] Filed: Jul. 19, 1995

[30] Foreign Application Priority Data

Aug. 10, 1994 [JP] Japan ..................... 6-210484

[51] Int. Cl.$^6$ ..................... A61B 3/02
[52] U.S. Cl. ............ 351/232; 351/237; 351/239; 351/243
[58] Field of Search .................... 351/237, 243, 351/245, 215, 220, 232, 222, 239, 234, 221, 217, 235

[56] References Cited

U.S. PATENT DOCUMENTS

| 4,298,253 | 11/1981 | Tagnon | 351/222 |
| 4,753,527 | 6/1988 | Ishihara | 351/244 |
| 5,444,504 | 8/1995 | Kobayashi et al. | 351/232 |

FOREIGN PATENT DOCUMENTS

| 0229570 | 7/1987 | European Pat. Off. . |
| 2461316 | 1/1981 | France . |
| 853329 | 10/1952 | Germany . |
| 3444580 | 6/1986 | Germany . |
| 4-347125 | 2/1992 | Japan . |

*Primary Examiner*—Hung X. Dang
*Attorney, Agent, or Firm*—Rossi & Associates

[57] ABSTRACT

A visual function examination apparatus, comprising an optotype presenting device for presenting optotypes for use in examinations of visual functions of examinee's eyes, for examining visual functions of the eyes by delivering luminous flux via reflecting system from the optotype presenting device, wherein the optotype presenting device is provided with optotypes for examinations to be carried out as the examinee opens his both eyes, the optotypes having polarizing plates, and a binocular fixation target which should become fusion impulse to binocular vision is disposed around the optotypes for examinations.

7 Claims, 10 Drawing Sheets

F I G . 8
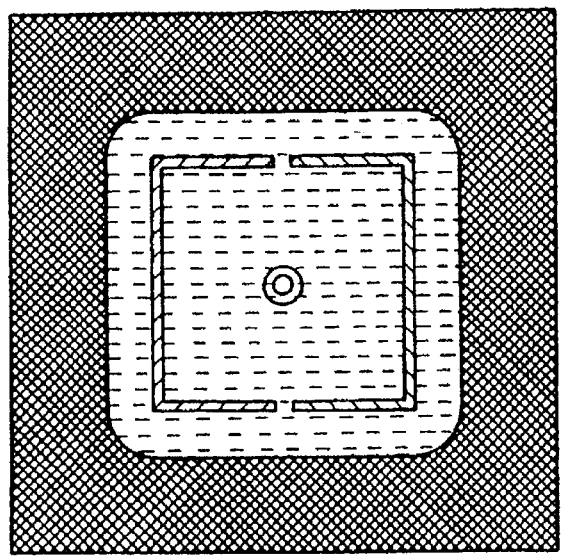
F I G . 9
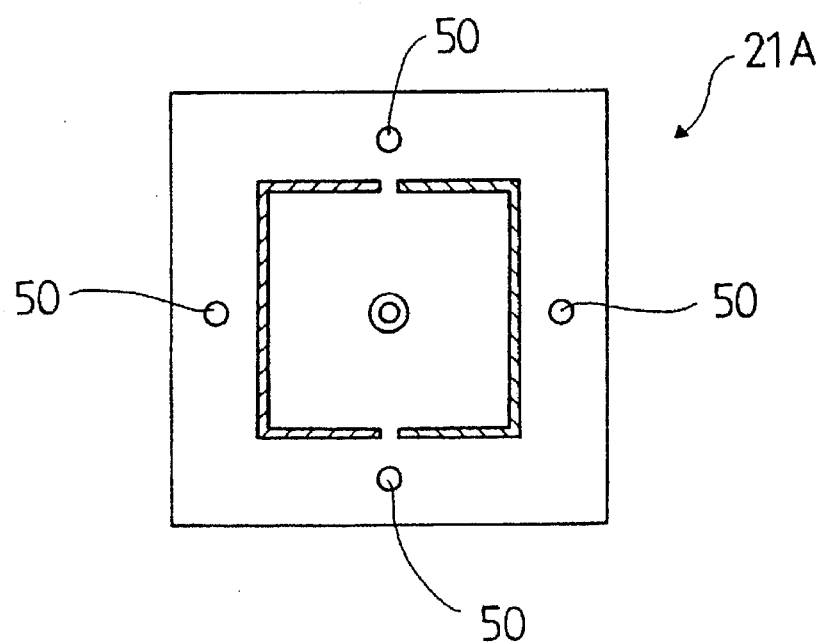

VISUAL FUNCTION EXAMINATION APPARATUS INCLUDING BINOCULAR FIXATION TARGET

BACKGROUND OF THE INVENTION

1. Field of the Invention

The present invention relates to a visual function examination apparatus for examining visual functions of eyes of an examinee.

2. Description of Related Art

Examinations of visual functions of examinee's eyes, for example, heterophoria measurement and the like, use optotypes which are placed at a predetermined distance (5 meters in general) from the eyes to be examined and are carried out by allowing the examinee to recognize those optotypes.

In recent years, in order to reduce space required for eye examinations, known is an examination apparatus which utilizes reflection by mirrors disposed inside a housing of the apparatus thereby to optically have a sufficient examining distance.

In such an apparatus, however, only optotypes can commonly be viewed inside of a housing which is dark as insulated from the outside. This causes a problem that a sense of distance is different from the case of recognition of optotypes actually disposed at a predetermined distance in a bright room, so that in the case of binocular examinations, binocular fixation may not be stable.

For example, optotypes for aniseikonia examinations may not allow fixation to fix at a desired position, and a figure which can be viewed by only a left eye and another which can be viewed by only a right eye are fused, as a result, accurate examinations of aniseikonia can not be achieved.

SUMMARY OF THE INVENTION

The present invention has been made in view of the above circumstances and has an object to overcome the above problems and to provide a visual function examination apparatus capable of examining visual functions of eyes to be examined, even if using optotypes provided inside a housing of the apparatus, with almost equivalent precision to that of an apparatus which presents optotypes at an actual predetermined distance in a bright room.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a visual function examining apparatus of this invention comprising an optotype presenting device for presenting optotypes for use in examinations of visual functions of examinee's eyes, for examining visual functions of the eyes by delivering luminous flux via reflecting means from the optotype presenting device, wherein the optotype presenting device is provided with optotypes for examinations to be carried out as the examinee opens his both eyes, the optotypes having polarizing plates, and binocular fixation means which should become fusion impulse to binocular vision is disposed around the optotypes for examinations.

According to the present invention, in the visual function examination apparatus which is provided with an optotype presenting device for presenting optotypes for visual function examinations, reflecting means for delivering luminous flux from the optotype presenting device to eyes to be examined in order to examine visual functions of the eyes, if providing binocular fixation targets around examination optotypes, examinations can be carried out with substantially the same accuracy as an apparatus which presents optotypes at an actual predetermined distance in a bright room.

Also in the case of optotypes for visual acuity examinations, uniocular visual acuity examinations can be performed in a state of the visual axis being stable as the examinee opens his both eyes.

BRIEF DESCRIPTION OF THE DRAWINGS

The accompanying drawings, which are incorporated in and constitute a part of this specification illustrate embodiments of the invention and, together with the description, serve to explain the objects, advantages and principles of the invention. In the drawings.

FIG. 8 is an optotype in form of a hollow frame shown in FIG. 7;

FIG. 9 is optotype for aniseikonia, projected on a screen according to a fourth embodiment of the present invention;

DETAILED DESCRIPTION OF THE PREFERRED EMBODIMENTS

A detailed description of preferred embodiments of a visual function examining apparatus embodying the present invention will now be given referring to the accompanying drawings.

Figure 1:
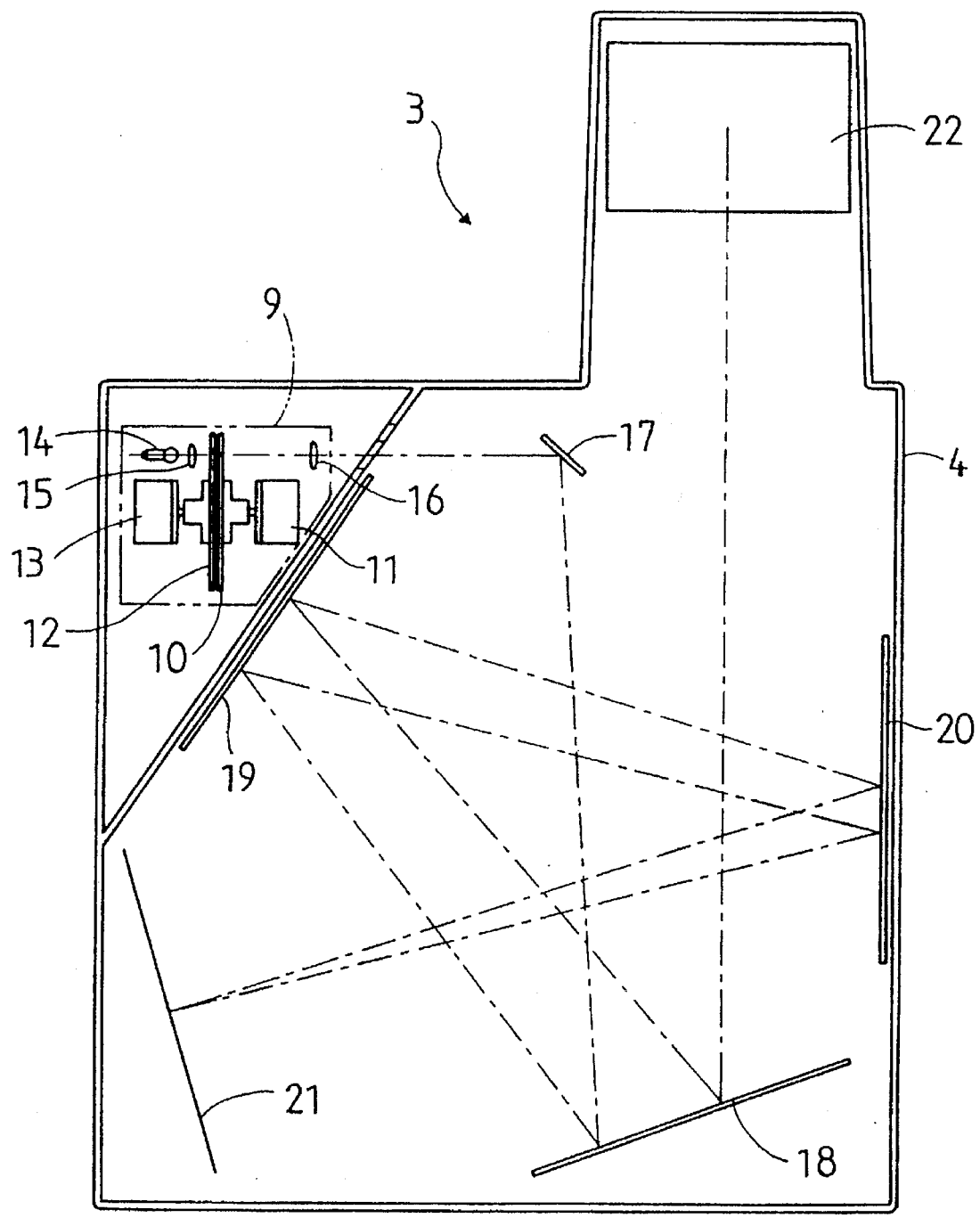
FIG. 1 is a schematic perspective front view of an arrangement of the optical system in an apparatus according to the first embodiment of the present invention.
Figure 2:
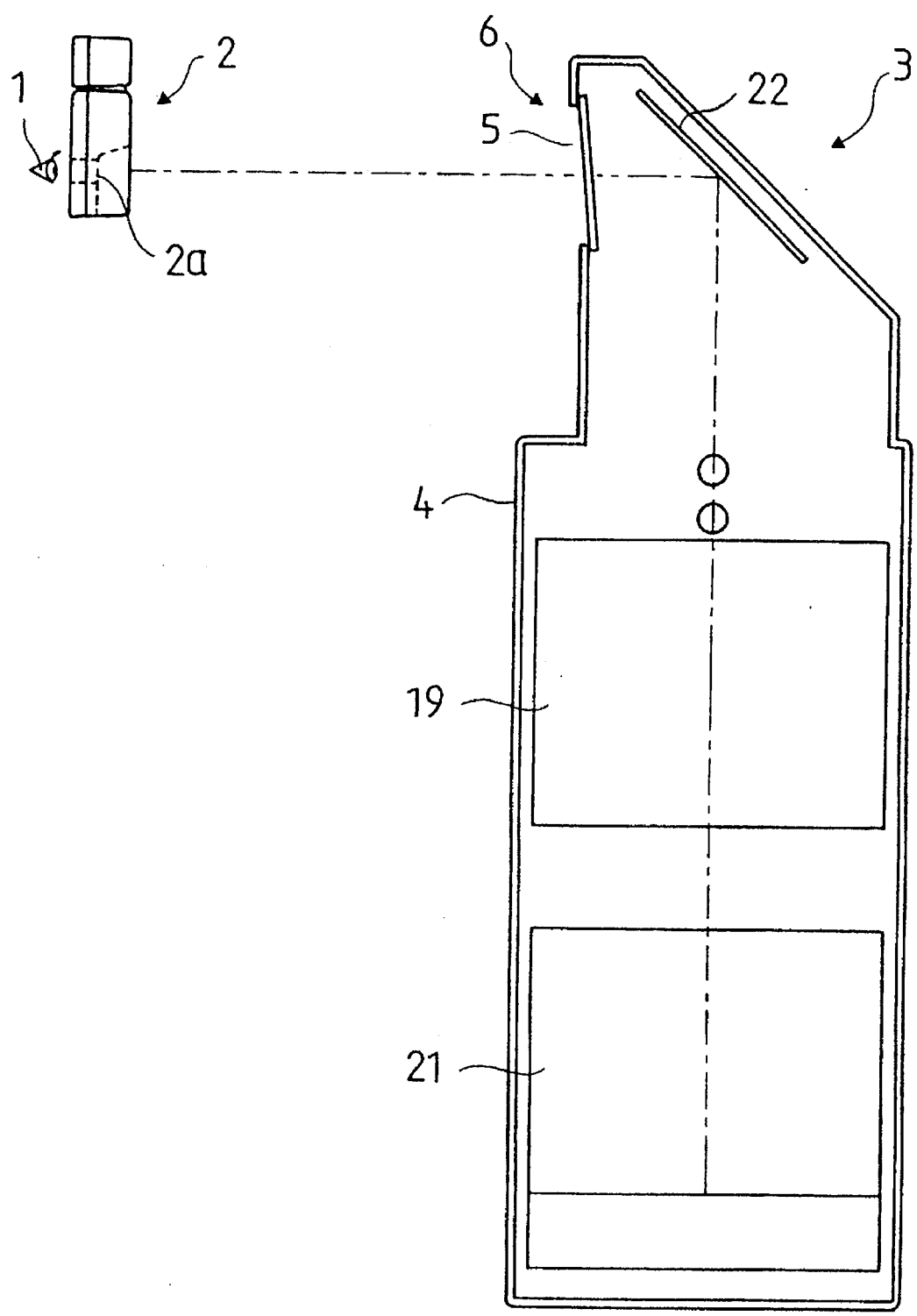
FIG. 2 is a schematic perspective side view of the arrangement of the optical system in the apparatus according to the first embodiment.

FIG. 1 is a perspective front view showing an arrangement of an optical system of the apparatus in the first embodiment. FIG. 2 shows the optical system from the left side of the apparatus of FIG. 1.

Numeral 1 is an eye to be examined. Numeral 2 is a subjective type of refractive power measuring device having right and left windows 2a on which optical elements having various optical characteristics are to be mounted, those optical elements being exchangeable. Numeral 3 is an optotype presenting device which is to be placed in front of the eye 1. The optotype presenting device 3 has a housing 4 which covers the interior components thereof and has an opening 6 in a side wall facing to the eye 1, the opening 6 being covered with a transparent protective glass 5. The examinee can view through the opening 6 optotypes which should be presented in the interior of the housing 4.

An optotype projecting unit 9 disposed in the housing 4 is constructed of an optotype disc plate 10 made of glass and the like on which many optotypes, such as optotypes for binocular vision examinations, are provided in a circle by means of chrome evaporation and the like. Those optotypes will be described later. The optotype disc plate 10 is rotated by a motor 11 to change an optotype to be presented to the examinee. The optotype disc plate 10 is partially masked with a mask plate 12 which is rotated by a motor 13 to cover a desired part of the disc plate 10. Also provided are an illumination lamp 14 for projecting an optotype for examination, a light condensing lens 15 and a projecting lens 16. Light emitted from the illumination lamp 14 is condensed by the condenser lens 15 to illuminate the optotype on the disc plate 10 and then projected by the projecting lens 16 toward a mirror 17.

Luminous flux projected from the optotype projecting unit 9 is reflected by mirrors 17, 18, 19 and 20 in turn to form an image of the optotype on a screen 21. Then luminous flux of the image is reflected by the screen 21, mirrors 20 and 19 in turn and reflected upward by the mirror 18, and reflected by a mirror 22 toward the eye 1 outside the optotype presenting device 3.

Figure 3:
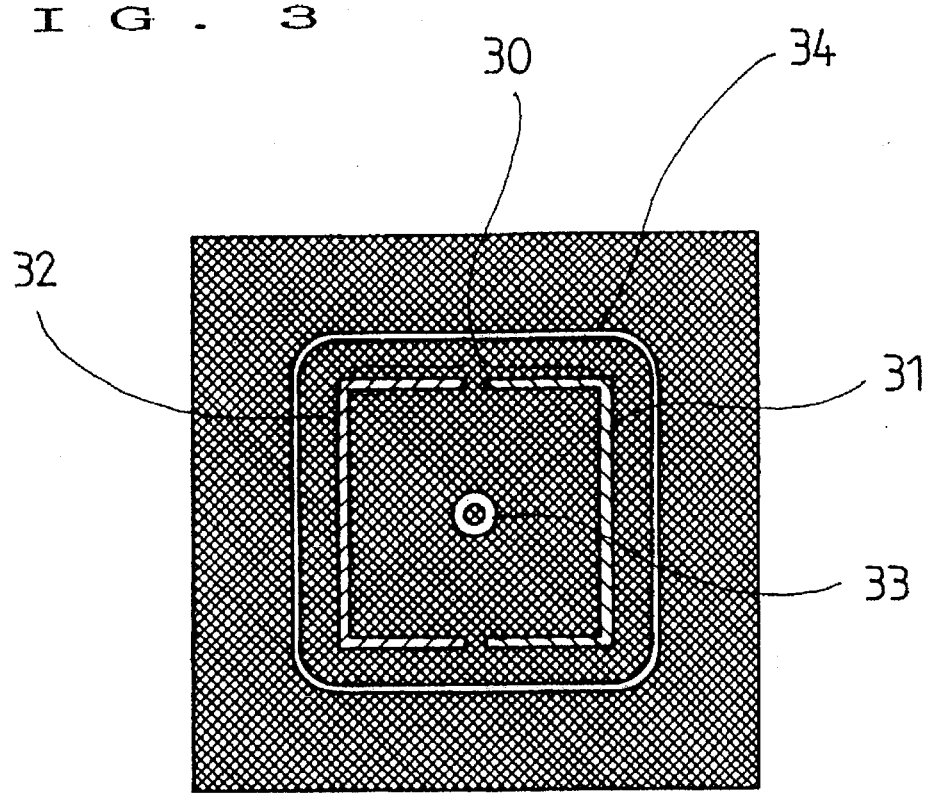
FIG. 3 is optotypes for aniseikonia, which is an example of optotypes for binocular vision examinations.

Next, the construction of optotypes for a binocular vision examination provided on the optotype disc plate 10 will be described hereinafter. FIG. 3 shows one of the optotypes, namely, an optotype called aniseikonia chart. This aniseikonia chart 30 is constituted of a right mark 31 in form of "]", a left mark 32 in form of "[" and a ring mark 33 positioned in a center therebetween. On the marks 31 and 32, polarizing plates having different polarizing angles are adhered respectively so as not to cover the ring mark 33, one of the polarizing plates having a polarizing angle of 135° and another having a polarizing angle of 45° crossing thereto. The ring mark 33 is a transparent area, thereby enabling recognition by both eyes of the examinee. A frame optotype 34 is provided around the aniseikonia chart 30 and serves as a binocular fixation target, being a light transparent area as well as the ring 33.

A visual function examination using the aniseikonia chart 30 is carried out as follows.

An examiner first operates the subjective type refractive power measuring device 2 with the control board not illustrated to put a polarizing plate having a polarizing angle of 135° onto a right eye examination window and another polarizing plate having a polarizing angle of 45° onto a left eye examination window respectively. When the examinee views the aniseikonia chart presented through each polarizing plate disposed on each examination window, then he should view the mark 31 by only his right eye and the mark 32 by only his left eye. The ring mark 33 and the frame optotype 34 are recognized by both eyes of the examinee. The visual function examination on aniseikonia is accordingly performed by comparing longitudinal size of the FIG. 31 and 32 which are recognized separately by each of the right and left eyes of the examinee. At this time, the frame optotype 34 will be fusion impulse to both eyes, thereby preventing those FIGS. 31 and 32 from fusing. Thus, accurate examinations on aniseikonia can be carried out.

The frame optotype 34 which serves as a binocular fixation target can produce the same effect as above if it is provided on various optotypes for binocular vision examinations besides the above aniseikonia chart 30, for instance, cross heterophoria optotype, etc.

When the frame optotype 34 is provided on optotypes for visual acuity examinations, such as Landolt ring charts, it enable uniocular visual acuity examinations as an examinee opens his both eyes. Optotypes for visual acuity examinations will be constructed as below.

Figure 4:
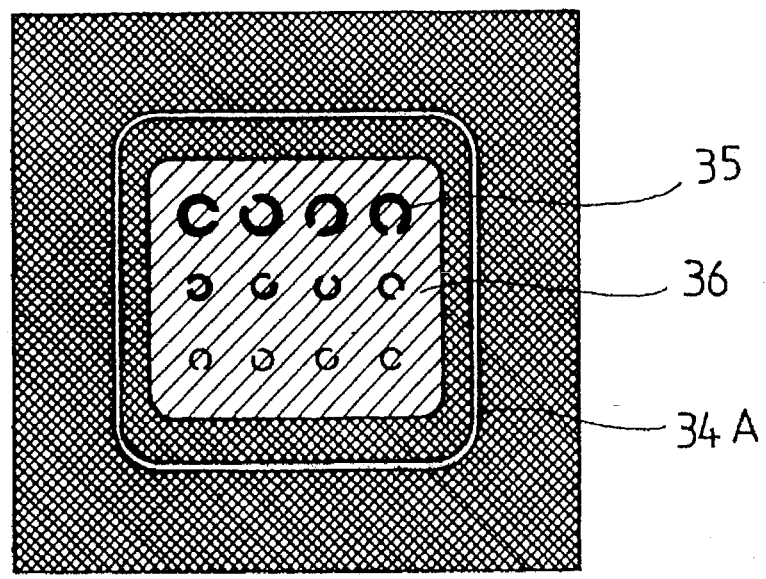
FIG. 4 is a chart in which a plurality of Landolt rings for a visual acuity value are presented.

FIG. 4 shows a state presenting a plurality of Landolt rings for a visual acuity value. Landolt rings 35 are drawn on the disc plate 10 by chrome evaporation, this embodiment using twelve Landolt rings. Numeral 36 indicates an area where a polarizing plate having a polarizing angle 45° is adhered on the front surface of the Landolt Pings 35. A frame optotype 34A transmits light and serves as a binocular fixation target.

The visual acuity examination using the optotypes constructed above is carried out as follows. When a polarizing plate having a polarizing angle 45° is disposed on the right eye examination window of the subjective type refractive power measuring device 2 and another polarizing plate having a polarizing angle 135° on the left eye examination window, a linearly polarized light having a polarizing angle 45° owing to the area 36 can reach to the right eye of the examinee, but it can not reach to the left eye. Accordingly, the examinee can view by only the right eye Landolt rings 35 in the area 36 illuminated. The frame optotype 34A is recognized also by the left eye, so that the binocular visual axis can be kept stable. Accordingly, uniocular visual acuity examinations can be conducted as the examinee opens his eyes.

When examining the left eye, the polarizing plates to be disposed on the examination windows of the subjective type refractive power measuring device 2 should be exchanged.

The frame optotypes 34 and 34A in the first embodiment are not limited to a frame shape, and other shapes may be used.

(Second Embodiment)

The first embodiment uses a frame optotype drawn together with optotypes on the disc plate 10 as binocular fixation target, instead thereof, the second embodiment uses a second optotype presenting means to form binocular fixation targets on the screen 21.

Figure 5:
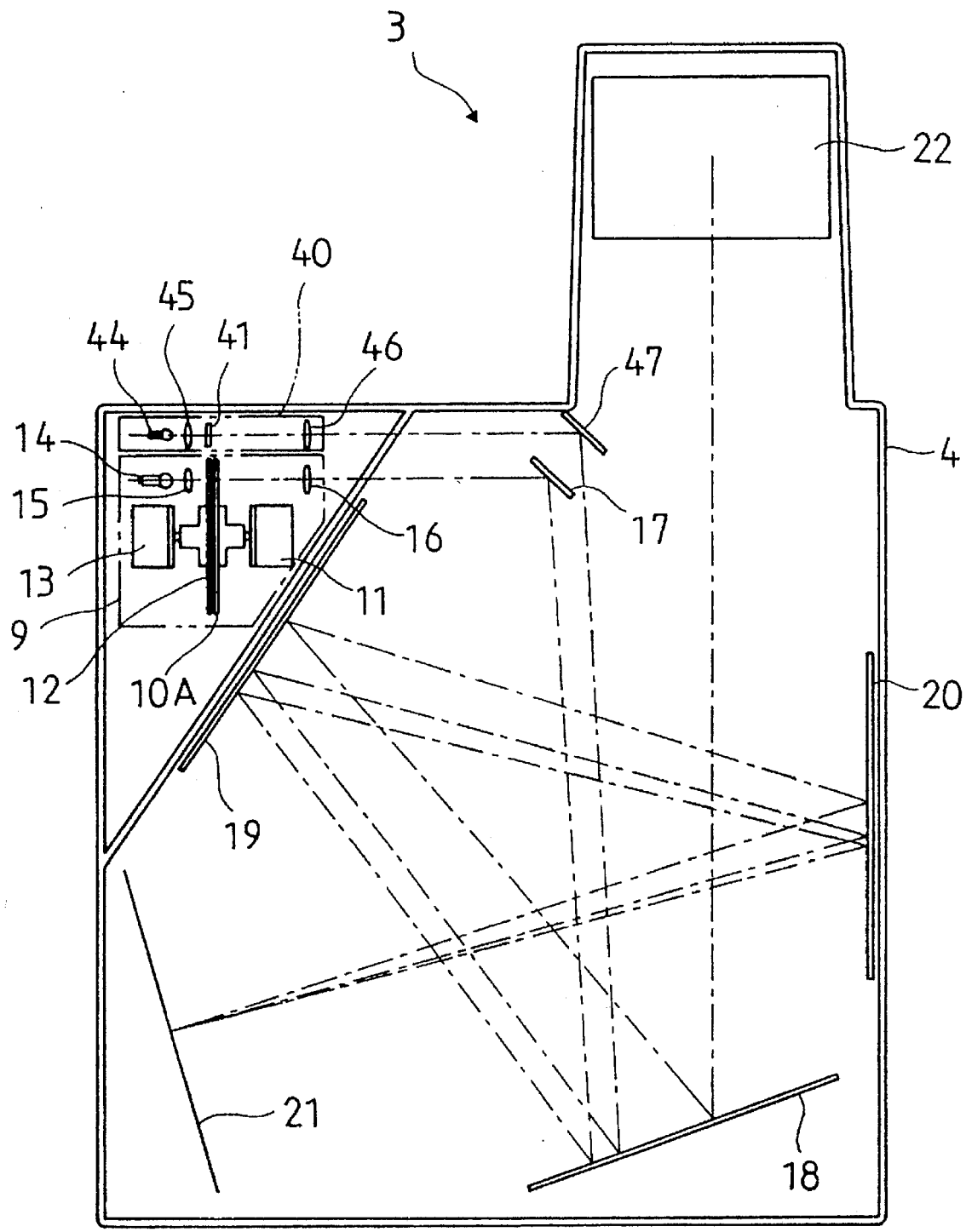
FIG. 5 is a schematic perspective front view of an arrangement of the optical system in all apparatus according to a second embodiment of the present invention.

FIG. 5 shows a perspective front view of the apparatus of the second embodiment, in which identical or similar parts to in the first embodiment are provided with the same reference numbers and duplicate descriptions thereof are omitted herein.

Figure 6:
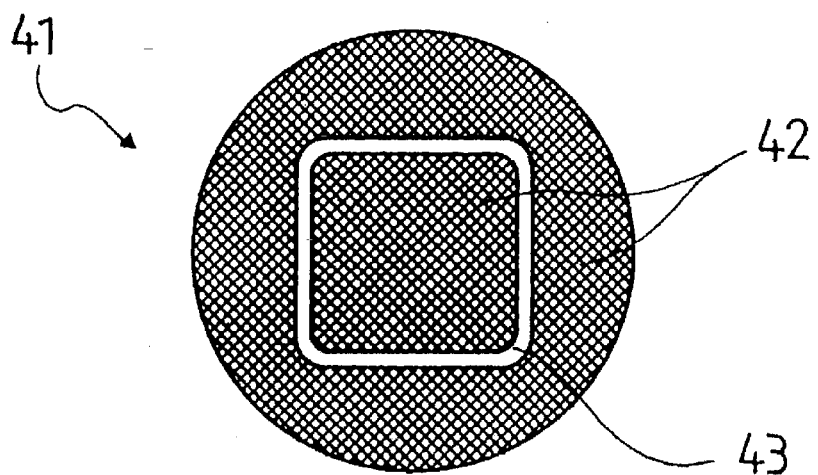
FIG. 6 is a construction of an optotype disc plate to be arranged in the second optotype projecting unit.

The second optotype projecting means 40 is constructed of an optotype plate 41, an illumination lamp 44, a condenser lens 45 and a projecting lens 46. The optotype plate 41 has an area 42 which shades light and a fixation frame optotype 43 which transmits luminous flux, as shown in FIG. 6.

Light emitted from the illumination lamp 44 is condensed by the condenser lens 45 to illuminate the optotype plate 41. Light passed through the optotype plate 41 is projected by the projecting lens 46, via mirrors 47, 18, 19 and 20 in turn, onto the screen 21. Image of the fixation frame optotype 43 (shown in FIG. 6) of the optotype plate 41 is projected so as to superimpose on the image of the optotype of the disc plate 10A illuminated by the illumination lamp 14. Thus, it can present to the examinee the optotype which serves as a binocular fixation target as well as the frame optotype 34 of the first embodiment.

In the second embodiment, accordingly, it is possible to superimpose an optotype which serves as a binocular fixation target onto a plurality of optotypes without adding any processing to the examination optotypes provided on the disc plate 10A. This can save having to adhere polarizing plates on the disc plate 10A as required in the first embodiment apparatus.

Providing of the optotype for a binocular fixation target may freely be selected by turning the illumination lamp 44 on or off.

(Third Embodiment)

Figure 7:
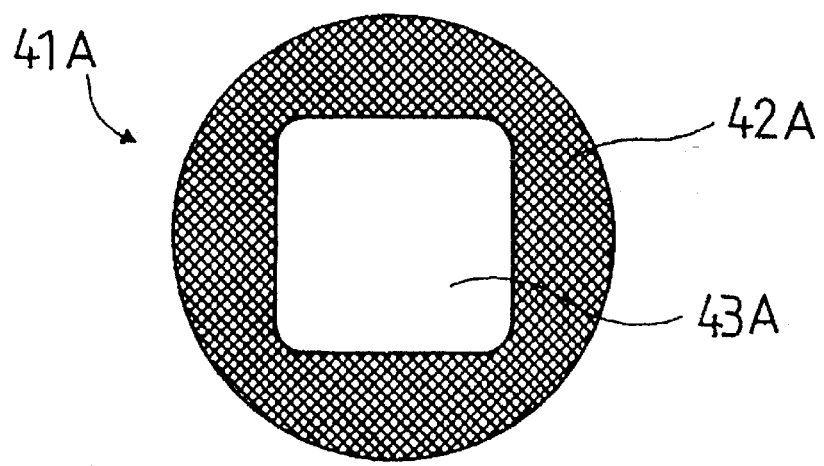
FIG. 7 is another construction of an optotype plate according to a third embodiment, which is used in the apparatus of the second embodiment.

The third embodiment is a different example of fixation targets to be used in the apparatus of the second embodiment. The optotype plate 41A in the third embodiment is constituted of a light shading area 42A and a hollow frame optotype 43A through which luminous flux can transmits, as shown in FIG. 7. It is preferably to adjust illuminance of the frame 43A projected on the screen 21 so as to be not much bright, more preferably, to about one tenth with respect to that of the image of the examination optotype (the ring mark 33). The adjustment of illuminance can be carried out by adjusting light quantity of the illumination lamp 44 or by providing a filter on the light path.

Accordingly, in such a construction of the optotypes, the examinee can recognize images of examination optotypes within the image of the hollow frame 43A. The image of the frame 43A provides light entirely over examination optotypes within a dark visual field, so that a boundary appears between the hollow frame 43A and the dark area. This boundary is used as a binocular fixation target (see FIG. 8).

Optotype presentation in the third embodiment will produce substantially the same effects as that, when an examination optotype is projected through an optotype projecting device onto a reflecting screen plate disposed at an actual desired distance in a bright room, the outline of the reflecting screen plate will be a binocular fixation target because of its reflectance difference from that of a background.

(Fourth Embodiment)

Although the first through third embodiments used fixation optotypes projected on the screen as binocular fixation targets, the fourth embodiment uses light sources disposed on the screen as fixation targets.

FIG. 9 shows a screen 21A on which examination optotypes of an aniseikonia chart are projected. Other constructions are omitted in the present embodiment, being similar as the first embodiment.

Numeral 50 are LEDs of light sources. The screen 21A are provided with four holes around images of the optotypes projected thereon. The LEDs 50 are disposed behind the screen 21A so as to appear only each head portion from the surface of the screen 21A. Combining with the examination optotypes as presented, light of the LEDs 50 turned on become binocular fixation targets. When LEDs 50 being off, LEDs 50 can not be recognized by the examinee because they are located at a dark place.

(Fifth Embodiment)

Figure 10:
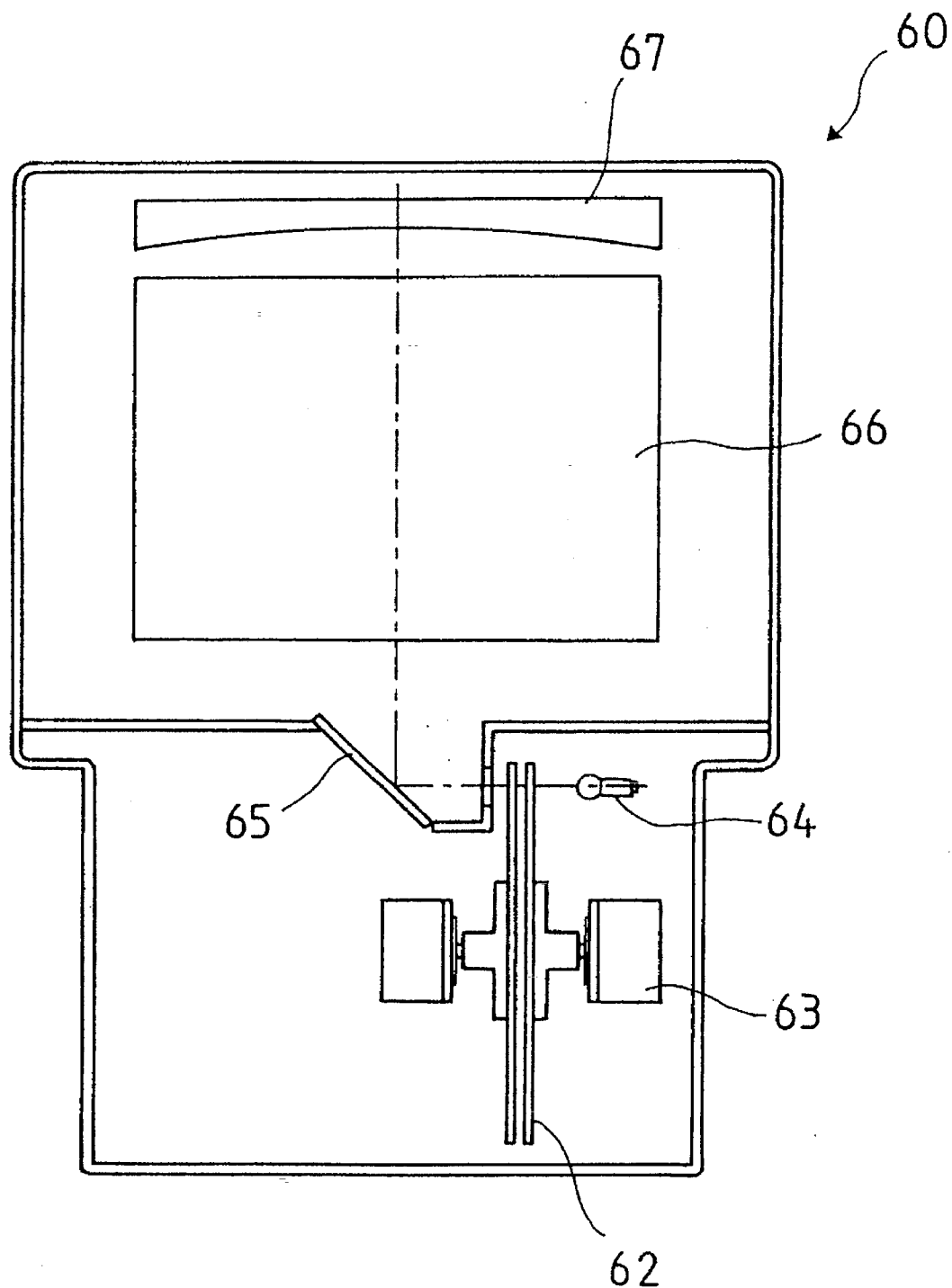
FIG. 10 is a schematic perspective front view of an apparatus according to a fifth embodiment.
Figure 11:
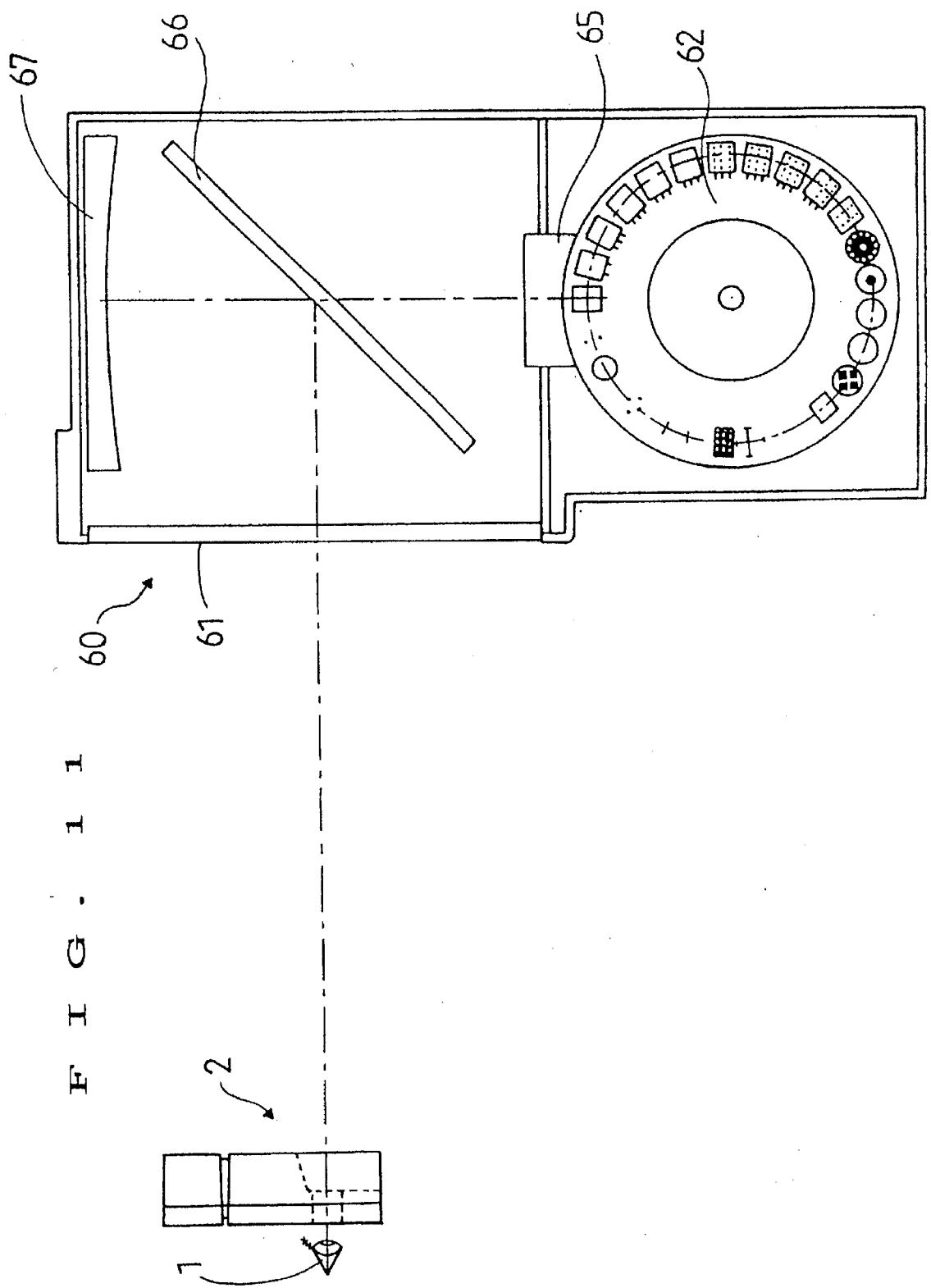
FIG. 11 is a schematic perspective side view of the apparatus according to the fifth embodiment.

The fifth embodiment uses an apparatus having a different optical system from the above first through fourth embodiments. FIG. 10 shows a perspective front view of the apparatus and FIG. 11 shows a perspective right side view of same.

Numeral 60 is an optotype presenting device in the present embodiment, provided with a window 61 in a side facing to examinee's eyes. The examinee can view optotypes through the window 61 during examination. The inside of the device 60 is painted black in order to make the interior structure hard to look by the eye 1 to be examined.

The optical system disposed inside the optotype presenting device 60 is constructed of, mainly, an optotype disc plate 62, an illumination lamp 64, a mirror 65, a half mirror 66 and a concave mirror 67.

The optotype disc plate 62 on which many examination optotypes are drawn is rotated by a motor 63 to change an examination optotype to be presented. Luminous flux of the optotype illuminated by the illumination lamp 64 is reflected by the mirror 65 upward, transmits through the half mirror 66 and reflected by the concave mirror 67 to magnify. The luminous flux reflected as magnified by the concave mirror 67 is reflected by the half mirror 66 and through the examination windows of the subjective type refractive power measuring device 2 to the eye 1 to be examined. The optical system is designed so that the optical distance between optotypes and the eye to be examined may become a predetermined distance (5 meters in general).

It is possible to add a frame optotype serving as a binocular fixation target on the optotype disc plate 62 as similar as in the first embodiment, even in the device having the above constructed optical system of the fifth embodiment.

Figure 12:
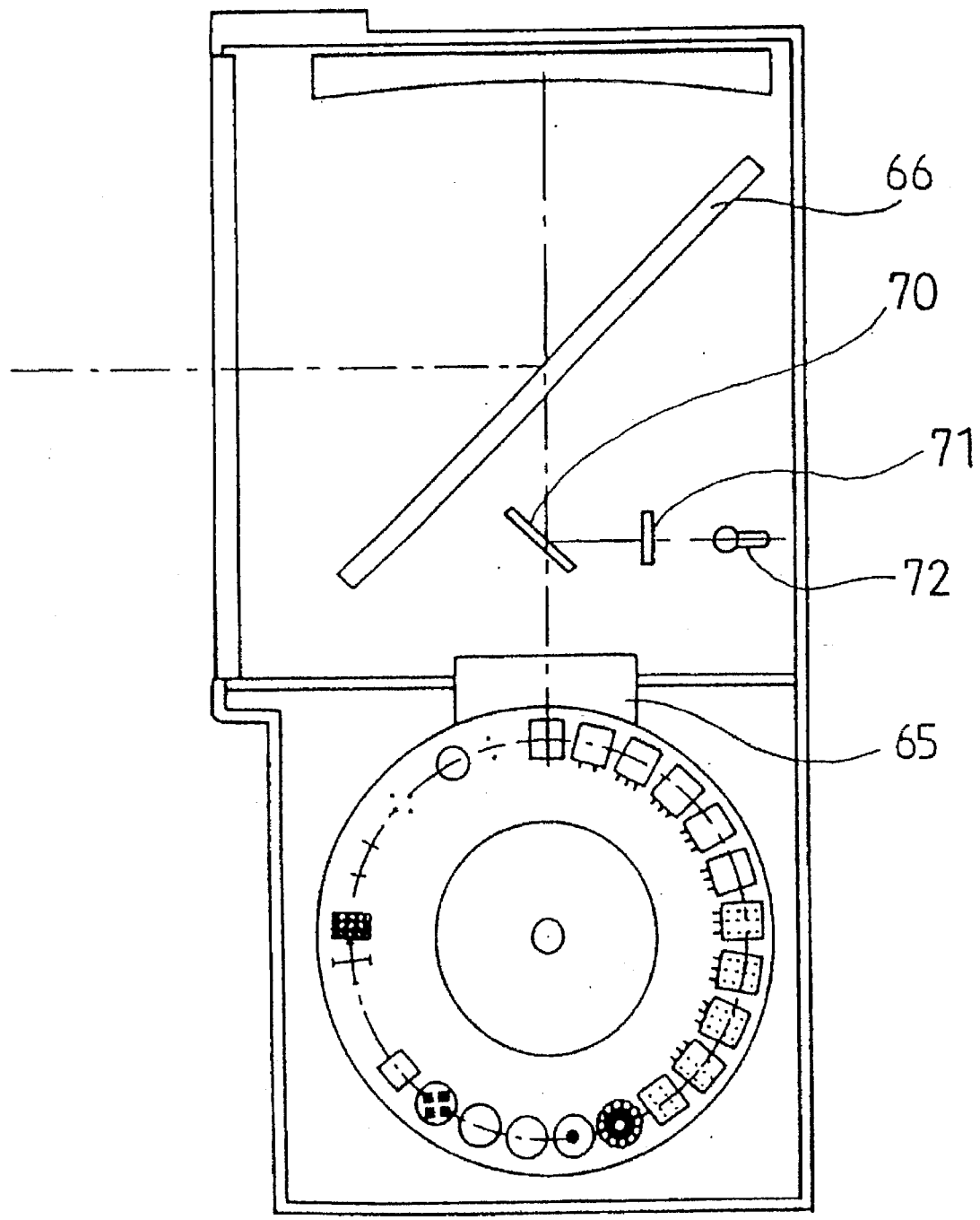
FIG. 12 is a schematic perspective view of an arrangement of the optical system of the fifth embodiment in a case of constructing binocular fixation targets as similar as the second or third embodiment.

It is also possible to superimpose luminous flux of binocular fixation targets on luminous flux of examination optotypes if providing, as shown in FIG. 12, another half mirror 70 on the optical path between the mirror 65 and the half mirror 66, an optotype plate 71 which has optotypes being binocular fixation targets as well as in the second and third embodiments on the reflecting optical path of the half mirror 70, and an illumination lamp 72 to illuminate the optotype plate 71.

Figure 13:
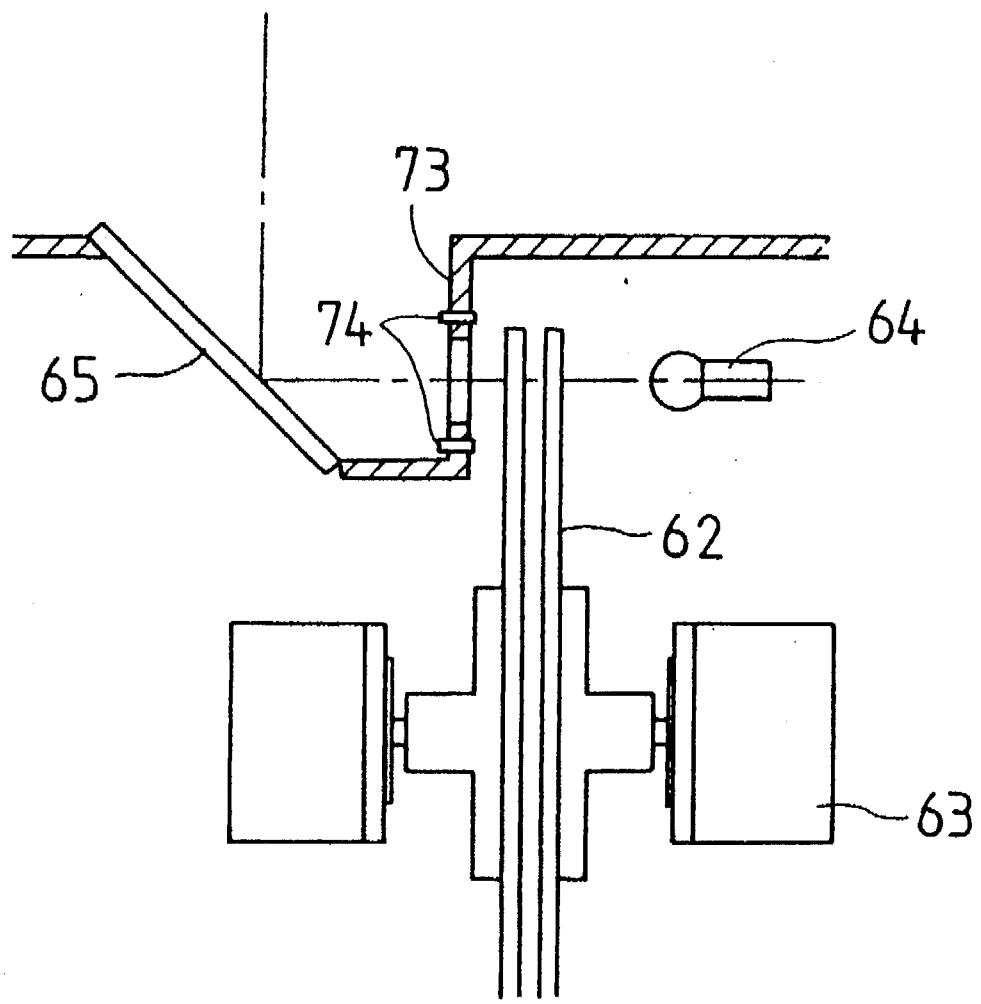
FIG. 13 is an arrangement of the optical system of the fifth embodiment in a case of constructing binocular fixation targets as similar as the fourth embodiment.

If disposing LEDs 74 in a partition board 73 which locates in just front of the optotype disc plate 62 as shown in FIG. 13, light emitted from the LEDs 74 can serve as binocular fixation targets as well as in the fourth embodiment.

Although the above mentioned embodiments relate to optotypes for an aniseikonia examination or a uniocular visual acuity examination to be carried out as an examinee opens his both eyes, other binocular examination optotypes, for instance, cross optotypes for position examinations, cross optotypes affixed with a fixation point and cyclophoria optotypes, etc. can produce substantially the same effects as the optotypes in the aforesaid embodiments.

In the second through fourth embodiments providing binocular fixation targets by using light sources separately from one for the examination optotypes, if control means to turn on the light source for the targets is additionally provided, automatic presentation of binocular fixation targets can be conducted according to examination optotypes to be required.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A visual function examination apparatus, comprising:

an optotype presenting device for presenting optotypes for use in examinations of visual functions of examinee's eyes; and means for delivering luminous flux from said optotype presenting device to the examinee's eyes;

wherein said optotype presenting device includes examination optotypes for examinations to be carried out when the eyes of the examinee are open, the examination optotypes comprising polarizing plates and a binocular fixation target, which should become fusion impulse to binocular vision, disposed around said examination optotypes.

2. A visual function examination apparatus according to claim 1, wherein said binocular fixation target comprises a frame optotype which surrounds said examination optotypes.

3. A visual function examination apparatus according to claim 2, wherein said frame optotype comprises a hollow frame optotype which surrounds said examination optotypes, the hollow frame optotype having lower illuminance than said examination optotypes.

4. A visual function examination apparatus according to claim 1, wherein said binocular fixation target comprises a plurality of light sources which are disposed substantially on an optotype presenting plane.

5. A visual function examination apparatus according to claim 1, wherein said binocular fixation target is constructed integratedly with said examination optotypes of said optotype presenting device.

6. A visual function examination apparatus according to claim 1, wherein said optotype presenting device comprises a projecting type of optotype presenting device and said binocular fixation target is projected so as to superimpose on a screen with said examination optotype.

7. A visual function examination apparatus comprising:

an optotype presenting device for presenting optotypes for use in examinations of visual functions of an examine's eyes and means for delivering luminous flux from said optotype presenting device to the examinee's eyes;

wherein said optotype presenting device is provided with examination optotypes for performing examinations of binocular visual functions, the examination optotypes including polarizing plates and a binocular fixation target, which should become fusion impulse to binocular vision, disposed around said examination optotypes.

* * * * *